US00PP13500P3

(12) United States Plant Patent
Meilland

(10) Patent No.: US PP13,500 P3
(45) Date of Patent: Jan. 21, 2003

(54) SHRUB ROSE PLANT NAMED 'MEIPRESTON'

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 09/759,263

(22) Filed: Jan. 16, 2001

(65) Prior Publication Data

US 2002/0095697 P1 Jul. 18, 2002

(51) Int. Cl.[7] ..... A01H 5/00
(52) U.S. Cl. ..... Plt./108

(58) Field of Search ..... Plt./108, 102, 141, Plt./150

*Primary Examiner*—Bruce R. Campell
*Assistant Examiner*—June Hwu
(74) *Attorney, Agent, or Firm*—Burns, Doane, Swecker & Mathis, LLP

(57) ABSTRACT

A new and distinct variety of landscape shrub rose plant is provided which forms in abundance semi-double blossoms in clusters that are ruby red in coloration. The vegetation is strong and vigorous. A dense and compact mounding shrub growth habit is displayed. Attractive dense medium green foliage with a satin finish is formed. Very good disease resistance is exhibited. Attractive ornamentation in the landscape is provided that is smaller and more compact than that provided by the 'Meikrotal' variety (U.S. Plant Pat. No. 6,087).

1 Drawing Sheet

BOTANICAL/COMMERCIAL CLASSIFICATION

*Rosa hybrida*/Landscape Shrub Rose Plant

VARIETAL DENOMINATION cv. 'Meipreston'

SUMMARY OF THE INVENTION

Figures 1, 2, 3, 4, 5, 6, 7, 8, 9, 10, 11, 12, 13, 14, 15, 16:
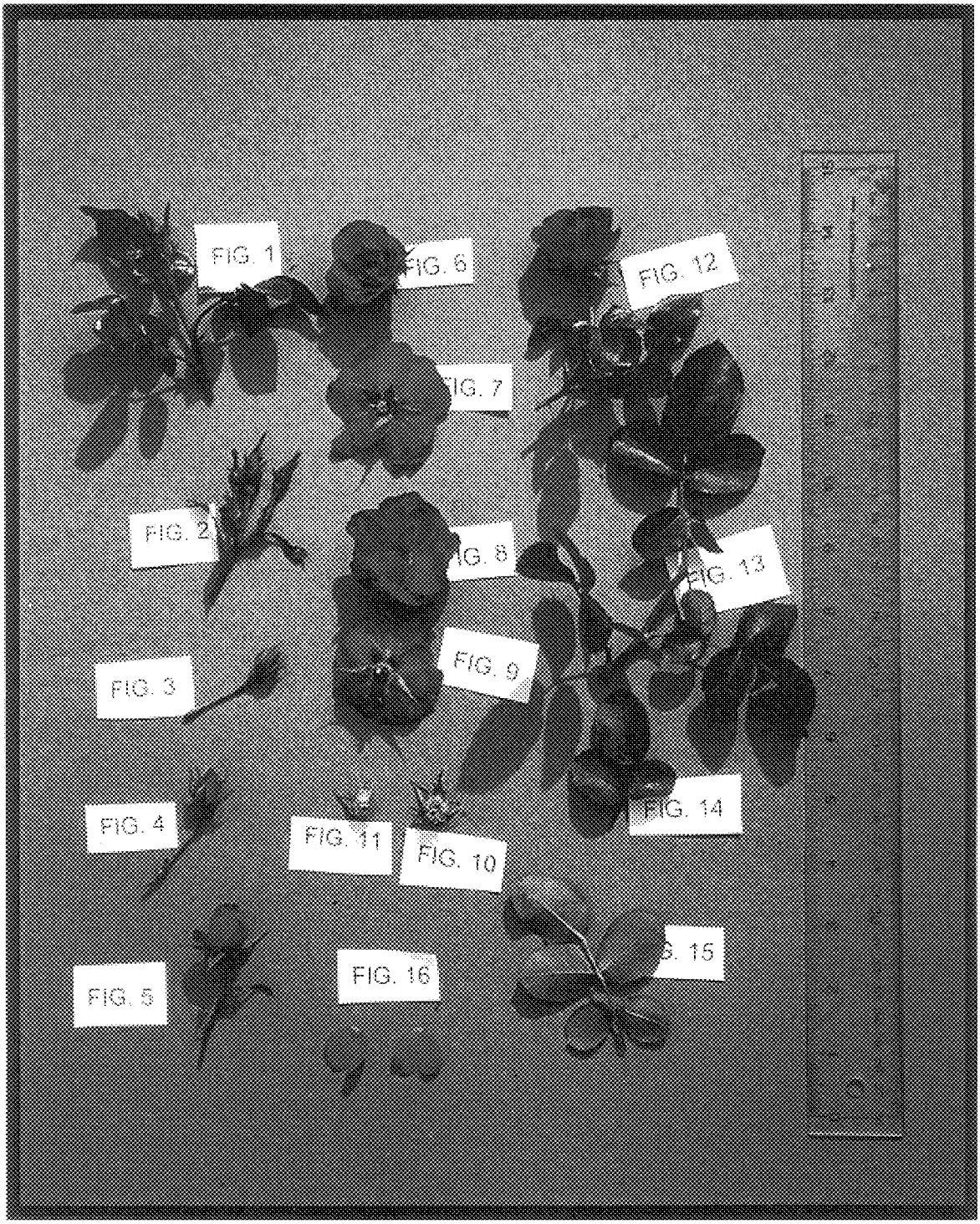

The new variety of *Rosa hybrida* landscape shrub rose plant of the present invention was created by artificial pollination wherein two parents were crossed which previously had been studied in the hope that they would contribute the desired characteristics. The female parent (i.e., the seed parent) of the new variety was the product of the cross of the 'Meineble' variety (U.S. Plant Pat. No. 7,116) and the 'Meikrotal' variety (U.S. Plant Pat. No. 6,087). The male parent (i.e., the pollen parent) of the new variety was the 'The Fairy' variety (non-patented in the United States). The parentage of the new variety can be summarized as follows:

('Meineble'×'Meikrotal')×'The Fairy'.

The seeds resulting from the above pollination were sown and small plants were obtained which were physically and biologically different from each other. Selective study resulted in the identification of a single plant of the new variety.

It was found that the new variety of landscape shrub rose plant of the present invention possesses the following combination of characteristics:

(a) abundantly forms in clusters attractive semi-double blossoms that are ruby red in coloration, (b) exhibits a compact mounding shrub growth habit, (c) forms vigorous vegetation, (d) forms dense medium green foliage with a satin finish, and (e) exhibits very good disease resistance.

The new variety well meets the needs of the horticultural industry. It can be grown to advantage as attractive dense and compact ornamentation in parks, gardens, public areas, and residential landscapes. It is particularly well suited for growing in the landscape where informal ornamentation is desired. The ruby red blossoms contrast nicely with the medium green foliage.

The new variety of the present invention forms a smaller and more compact plant than its 'Meikrotal' parent.

The characeristics of the new variety have been found to be homogeneous and stable and are strictly transmissible at West Grove, Pa. by asexual propagation such as budding, grafting, and cuttage from one generation to another. The plant propagates well on its own roots when propagated from cuttings.

The new variety has been named the 'Meipreston' variety. The new variety is being marketed under the RUBY MEIDILAND trademark.

BRIEF DESCRIPTION OF THE PHOTOGRAPH

The accompanying photograph shows, as nearly true as it is reasonably possible to make the same in a color illustration of this character, typical specimens of the plant and plant parts of the new variety. The rose plants of the new variety illustrated herein were three years of age and were grown outdoors during the fall on their own roots at West Grove, Pa. Dimensions in inches and centimeters are indicated at the right of the photograph.

FIG. 1—illustrates a specimen of a young shoot;

FIG. 2—illustrates a specimen of floral buds before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem with foliage;

FIG. 13—illustrates a specimen of a main branch with foliage;

FIG. 14—illustrates a specimen of a leaf with three leaflets—plan view—upper surface;

FIG. 15—illustrates a specimen of a leaf with five leaflets—plan view—under surface; and FIG. 16—illustrates specimens of maturing petals.

DETAILED DESCRIPTION

The chart used in the identification of colors is that of The Royal Horticultural Society (R.H.S. Colour Chart). The description is based on the observation of five year-old specimens of the new variety during August while grown outdoors on 'Dr. Huey' rootstock at West Grove, Pa. The plants received minimal supplemental water and minimal fertilization.

Class: Landscape Shrub Rose.

Plant:

*Height.*—Approximately 1 meter on average at the end of the growing season.

*Width.*—Approximately ⅔ meter on average at the end of the growing season.

*Habit.*—Compact and mounding.

Branches:

*Color.*—Young stems: Yellow-Green Group 144C with highlights of Red Group 53B. Adult wood: Yellow-Green Group 146B.

*Texture.*—Smooth.

*Thorns.*—Shape: needle-shaped as well as some bristles. A secreting gland commonly is present at the tip of the bristles. Size: the prickle-like thorns commonly measure approximately 5 mm in length on average. The bristles appear as stiff glandular hairs that commonly are approximately 0.1 to 0.8 mm in length (excluding gland). Quantity: the prickle-like thorns are moderately numerous, up to approximately 30 are present on a stem having a length of 30 cm. There commonly are approximately 10 to 20 bristles on a flowering stem having a length of 1 cm. Thorn color: near Greyed-Purple Group 184A to 185B when mature. Bristle color: believed to be near Greyed-Red Group 181C. The small size renders difficult the exact color determination.

Leaves:

*Stipules.*—Narrow and triangular with the auricle facing downward. The bud-end width commonly is 0.5 to 0.7 cm (approximately 0.6 cm on average) and the leaf-end width commonly is 0.5 to 1.0 cm (approximately 0.75 cm on average). The length commonly is 0.95 to 2.1 cm (approximately 1.4 cm on average). The color is near Yellow-Green Group 146C to 146D.

*Petioles.*—Color upper surface: Yellow-Green Group 144A. Color under surface: Yellow-Green Group 144C. Texture: smooth with some scattered stiff glandular hairs on both sides. Such hairs are more numerous on the ventral side both in and along the groove. Larger glandular hairs are present on the dorsal side.

*Leaflets.*—Number: 3, 5, and 7. Shape: ovate with rounded base and acute apices. Serration: regular. Texture: glabrous and lustrous. Overall appearance: dense, medium green in coloration, and leathery with a satin finish. Color (young foliage): upper surface: near Green Group 141B and 141C with highlights of Greyed-Purple Group 184B. under surface: Green Group 141C with highlights of Greyed-Purple Group 184B. Color (adult foliage): upper surface: Green Group 139A. Under surface: Yellow-Green Group 146B. Size: The terminal leaflet commonly ranges in length from 2.5 to 4.3 cm (approximately 3.8 cm on average), and commonly ranges in width from 1.8 to 2.8 cm (approximately 2.4 cm on average). The other leaflets commonly range in length from 1.2 to 3.3 cm (approximately 2.5 cm on average), and commonly range in width from 0.6 to 2.2 cm (approximately 1.8 cm on average).

Inflorescence:

*Number of flowers.*—Commonly approximately 1 to 8 and commonly in a cluster.

*Peduncle.*—Yellow-Green Group 144B with pubescence of White Group 155D, and approximately 3 cm in length on average.

*Sepals.*—Upper surface: Yellow-Green Group 144B with pubescence of White Group 155D. Under surface: Green Group 143B. Number: 5, 6, or 7, with 6 sepals being present approximately one-half the time, and 7 being present slightly more often than 5. Size: approximately 1.2 to 1.7 cm in length (approximately 1.4 on average), and approximately 0.45 to 0.65 cm in width (approximately 0.55 cm on average). Sepal extensions: commonly none up to 5 per sepal (approximately 2 on average). The extensions commonly range in length from 1.2 to 1.7 cm (approximately 1.4 cm on average), and range in width from 0.45 to 0.65 cm (approximately 0.55 cm on average).

*Buds.*—Shape: globose. Length: approximately 2 cm on average. Size: small to medium. Color (when opening): upper surface: Red Group 45B. under surface: Red Group 45A.

*Flower.*—Form: semi-double and cup-shaped. Diameter: approximately 4 cm on average. Color (when opening begins): upper surface: at the apex near and through Red Group 46B and 46C, and thereafter shading near and through Red Group 52B and 52C. under surface: near and through Red-Purple Group 58B. Color (when blooming): upper surface: at the apex near Red Group 46A, and thereafter shading to near and through Red Group 45A and 45B and Red Group 46B and 46C, and into and near Red Group 52B and 52C towards the base. Under surface: near and through Red-Purple Group 58B and 58C and Red Group 46B. Color (at end of blooming): upper surface: at the apex near Red Group 46A, and thereafter shading to near and through Red Group 45A and 45B and Red Group 46B and 46C, into and near Red Group 52B Band 52C towards the base. under surface: near and through Red-Purple Group 58B and 58C. Basal petal spot: present on both surfaces, the coloration is White Group 155B to 155D at the apical region, and Green-White Group 157C to 157D ending in Green-White Group 157B along the midrib at the base. Petal shape: oval to slightly obovate. Petal margin: entire.

Petal apex: broadly obtuse to slightly emarginate. There commonly is a small mucronate tip on most petals. On many petals the tip area is creased thereby causing the petals to appear to have a sinuate margin. Petal base: broadly cuneate. Petal number: commonly ranges from 8 to 27 (approximately 15 on average). Petal size: Commonly the length is 1.6 to 2 cm (approximately 1.8 cm on average), and the width is 1.2 to 2.2 cm (approximately 1.8 cm on average). Petal texture: smooth with some slight wrinking. The veins tend to be prominently depressed on both surfaces. Petaloid number: commonly 1 to at least 7 per bloom (approximately 3 per bloom on average). Petaloid size: commonly the length is approximately 6 to 17 mm (approximately 12 mm on average), and the width is approximately 3 to 10 mm (approximately 6 mm on average). Petaloid shape: some are sickle-like in shape with a base that is narrowly acute and an apex that is rounded to broadly acute. The apex is often bent over, and rudimentary stamenous tissue may be present on the convex side of such petaloid. Also, some petaloids are winged-shaped with rudimentary stamenous tissue located between two petal tissue areas. Petaloid color: substantially the same as the petals. However, in view of the significant narrowing of the base the spot at the base is greatly reduced and may even be absent. Sepalous petals: commonly none or up to 2 per bloom (approximately 1 on average). The coloration is substantially the same as the petals with some thickened green tissue over approximately 5 to 80 percent of the structure that is substantially the same coloration and texture as the sepals. Stamen number: approximately 120 on average. Anthers: Brown Group 200C in coloration. The length commonly is approximately 0.8 to 1 mm (approximately 0.83 mm on average), and the width commonly is approximately 0.5 to 0.7 mm (approximately 0.53 mm on average). Filaments: Greyed-Yellow Group 161C in coloration. The length commonly is 1.8 to 7.5 mm (approximately 3.5 mm on average). Pistils: approximately 36 on average. Stigmas: Yellow-White Group 158A in coloration. Styles: Yellow-White Group 158B in coloration. The length commonly is 5 to 7 mm (approximately 5.7 mm on average). Fragrance: none detected by casual olfactory examination. Petal drop: the petals commonly detach cleanly. Lasting quality: the blossoms commonly last approximately 10 to 18 days on the plant depending upon environmental conditions. Receptacle: Data at the time of fully open blooms is provided. The configuration is that of a straight-sided wine glass. The length is approximately 6.4 mm on average and the width is approximately 5 mm on average. Substantially glabrous and glaucous to glaucescent, occasionally 1 or 2 two stiff grandular hairs have been observed but usually are absent. The color with the glaucous bloom is near Green Group 138D and 139D. When the glaucous bloom is removed the color is near Green Group 141C, 143A, and 143B.

Development:

*Vegetation.*—Vigorous and strong.

*Blossoming.*—Abundant and everbearing.

*Hardiness.*—Has withstood −25° F. in U.S.D.A. Hardiness Zone 4b.

*Resistance to diseases.*—Very good with respect to Powdery Mildew (*Sphaerotheca pannosa*) and Black Spot (*Diplocarpon rosae*).

*Resistance to heat and drought.*—The plant performed well in the drought conditions of Eastern Pennsylvania. It continued to bloom well after several weeks of insignificant rainfall. Also, the plant continued to bloom well after repeated heat loads with temperatures exceeding 95° F. while combined with drought.

I claim:

1. A new and distinct variety of landscape shrub rose plant characterized by the following combination of characteristics:

(a) abundantly forms in clusters attractive semi-double blossoms that are ruby red in coloration, (b) exhibits a compact mounding shrub growth habit, (c) forms vigorous vegetation, (d) forms dense medium green foliage with a satin finish, and (e) exhibits very good disease resistance;

substantially as herein shown and described.

* * * * *